United States Patent
Van Rees

(10) Patent No.: US 6,245,291 B1
(45) Date of Patent: Jun. 12, 2001

(54) METHOD FOR DEODORIZING TOILETS

(76) Inventor: Norman A. Van Rees, 792 N. Ballas, Kirkwood, MO (US) 63122

( * ) Notice: Subject to any disclaimer, the term of this patent is extended or adjusted under 35 U.S.C. 154(b) by 0 days.

(21) Appl. No.: 09/387,380

(22) Filed: Sep. 2, 1999

Related U.S. Application Data

(63) Continuation of application No. 08/982,568, filed on Dec. 2, 1997, now Pat. No. 6,066,293, which is a continuation of application No. 08/546,522, filed on Oct. 20, 1995, now Pat. No. 5,709,872.

(51) Int. Cl.$^7$ ...................................................... A61L 11/00
(52) U.S. Cl. ............................. 422/5; 424/76.7; 424/76.8
(58) Field of Search ................................. 422/1, 5, 7, 14, 422/28; 514/77, 114; 510/384; 558/169; 424/76.7, 76.8

(56) References Cited

U.S. PATENT DOCUMENTS

| | | | |
|---|---|---|---|
| 3,970,576 | * | 7/1976 | Carmello et al. . |
| 4,107,312 | * | 8/1978 | Wegner et al. . |
| 5,650,402 | * | 7/1997 | Fost et al. .............................. 514/77 |

FOREIGN PATENT DOCUMENTS 7-197090 * 8/1995 (JP) .

* cited by examiner

Primary Examiner—Elizabeth McKane
(74) Attorney, Agent, or Firm—Armstrong Teasdale LLP

(57) ABSTRACT

A method for deodorizing toilets, and in particular the flushing fluid in a closed toilet system, includes the use of phospholipids in the fluid to kill or inhibit odor-causing microbes.

25 Claims, 2 Drawing Sheets

METHOD FOR DEODORIZING TOILETS

This application is a continuation application of U.S. patent application Ser. No. 08/982,568 filed Dec. 2, 1997, now U.S. Pat. No. 6,066,293, which is a continuation of U.S. patent application Ser. No. 08/546,522, filed Oct. 20, 1995, now U.S. Pat. No. 5,709,872.

This invention relates to deodorizing toilets, and in particular toilets which recirculate flushing fluid.

BACKGROUND OF THE INVENTION

In closed toilet systems, such as those used on airplanes, busses, and campers, the flushing fluid is recirculated. Recirculation of the flushing fluid requires that the used fluid be deodorized. Formaldehyde and glutaraldehyde have been used to disinfect flushing fluid. However, because of environmental concerns about the use of volatile organic compounds (VOCs), government regulations are increasingly restricting use of formaldehyde and glutaraldehyde.

Various attempts have been made to find alternative treatments for flushing fluids. Quaternary amines exhibit some antimicrobial action and thus have some ability to prevent the development of odors in the fluid, but are very irritating to the skin. Moreover, many of these compounds are corrosive, and their use in closed toilet systems is prohibited by many companies.

According to the principles of this invention, a toilet flushing fluid is made with phospholipids, and in particular synthetic phospholipids. These phospholipic compounds exhibit surf actant characteristics and are well tolerated by human tissue, i., they exhibit exceptionally low ocular irritation and oral toxicity. Synthetic phospholipids are generally characterized as having a quaternized alkyl amine groups and at least one phosphorus-containing anion in the molecule. Various synthetic phospholipids have been disclosed for example, in. U.S. Pat. Nos. 4,215,064, 4,233,192 and 4,380,637 to Lindemann et al., U.S. Pat. Nos. 4,209,449, 4,336,385 and 4,503,002 to Mayhew et al., and U.S. Pat. Nos. 4,243,602, 4,283,542 and 4,336,386 to O'Lenick et al.

There is a need to provide a method for deodorizing the fluid used in closed toilet systems such as those used in airplanes, busses, and campers, which does not rely upon VOCs, is safe for human contact, does not corrode the fixtures, yet effectively prevents odors from developing in the fluid. Generally, the method for deodorizing toilets according to the present invention achieves these goals by providing an effective amount of phospholipid in the flushing fluid to kill or inhibit odor-causing microbes. The present invention provides a method of powerfully deodorizing the flushing fluid that complies with current environmental regulations, and is well tolerated by human tissue.

These and other features and advantages will be in part apparent, and in part pointed out hereinafter.

DETAILED DESCRIPTION OF PREFERRED EMBODIMENT

Figure 1:
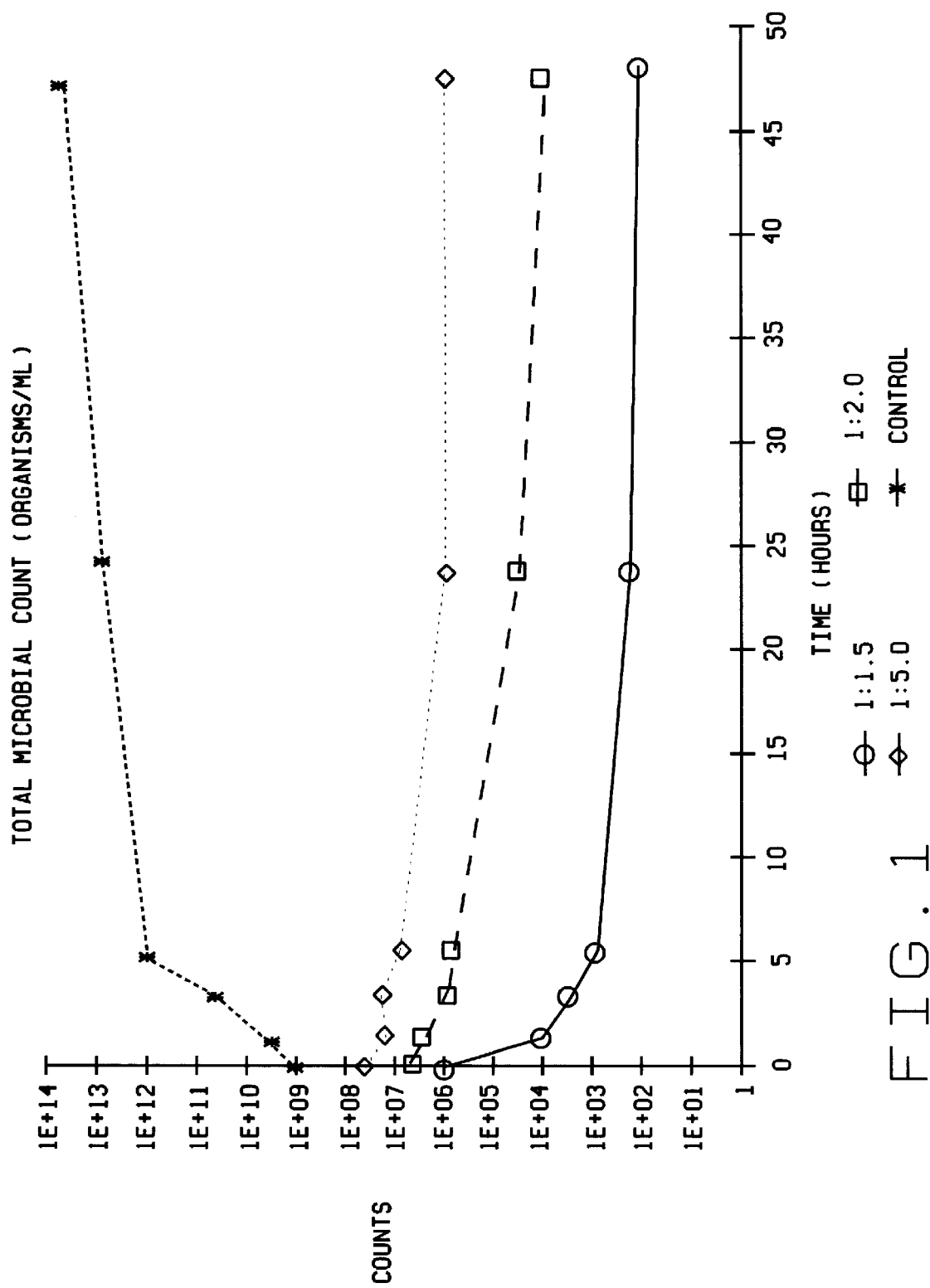
FIG. 1 is graph of microbial counts in various dilutions of a flushing fluid according to the principles of the present invention, showing the ability of these flushing fluids to control microbes.

The present invention provides for deodorizing toilets, and in particular for deodorizing the flushing fluid used in closed toilet systems, such as those used on airplanes, buses and campers. Generally, the method of this invention employs a toilet flushing fluid with a concentration of phospholipid effective to prevent odors from developing in the fluid by killing bacteria in the fluid or at least inhibiting the propagation of bacteria in the fluid. The flushing fluid may also contain a deodorant or scent to mask what odors do develop in the flushing fluid.

Examples of phospholipids useful in the present invention are as disclosed in U.S. Pat. No. 5,286,719, U.S. 5,215,976, U.S. 4,503,002 and U.S. 4,209,449, the disclosures of which are all incorporated herein by reference. Phospholipids useful in the present invention also include Phospholipid PTC™, Phospholipid EFA™, Phospholipid SV™, Phospholipid PTS, Phospholipid CDM™, Phospholipid PTL, and Phospholipid GLA available from Mona Industries, Inc., Paterson, N.J.

According to this invention, a phospholipid such as Phospholipid PTC™ is provided in the toilet flushing fluid in a concentration sufficient to kill or inhibit the propagation of odor-causing microbes. The phospholipid concentration is preferably between about 200 and about 7900 parts per million of the flushing fluid, and more preferably between about 400 and 2000 parts per million. Of course higher concentrations could be used but are believed to be unnecessary.

The flushing fluid is preferably formed by mixing a concentrate with tap water. A standard ratio is 1 oz. of concentrate per gallon of water, ie., 1:128. The phospholipid preferably makes up between about 6.50 and about 20.00 percent by weight of the concentrate. Water preferably constitutes the majority of the concentrate, ranging between about 67.93 and about 89.70 percent by weight of the concentrate. The concentrate may also include fragrance, such as Clean & Fresh, #2257 available from Chemia, Inc., St. Louis, Miss., in an amount ranging from about 2.31 to about 7.00 percent by weight, to give the fluid a clean, fresh fragrance, and mask what odors do develop in the flushing fluid. In a portable toilet application, an appropriate light "potpourri"-type fragrance may be used. In an industrial or institutional application, such as a public rest room on an airplane, a strong or, more effective odor-neutralizing fragrance may be used, such as citronella, mint, or spice. When the concentrate is a liquid form, the fragrance is preferably an anhydrous or nearly anhydrous liquid selected from the group of essential oils, aroma chemicals, and odor neutralizers and masks. The fragrance is preferably, but not necessarily, a biodegradable substance. The concentrate preferably also contains alcohol, such as isopropyl alcohol, in an amount ranging from about 1.32 to about 2.00 percent by weight, to help solubilize fragrances. In addition, a coloring agent such as FD&C Blue #1 or Acid Blue #9 may be added to the concentrate in an amount preferably ranging from about 0.06 to about 0.07 percent by weight, to produce a deep blue color. A deep blue color is preferred because it best masks urine and other substances in the flushing fluid. The color, like the fragrance, is preferably, but not necessarily, a biodegradable substance. A detergent, such as Surfonic N95 or Surfonic N120 can be added to increase the detergency (cleaning capability) of the fluid. Additional anti-microbial agents such as triclosan or ethylene glycol mono phenyl ether can be added to help control odor-causing microbes. The preferred concentration of triclosan in the flushing fluid is between about 1 and 20 parts per million. The preferred concentration of ethylene glycol mono phenyl ether is about 40 parts per million.

More specifically, the following are examples of concentrates useful in deodorizing toilets and in particular, airplane toilets, portable toilets and the like, according to this invention.

EXAMPLE 1

A toilet flushing fluid concentrate was prepared according to the following formula:
- 6.60 grams of Phospholipid PTCh from Mona Industries, Inc.
- 1.32 grams of isopropyl alcohol
- 2.31 grams of Clean & Fresh Fragrance #2257 from Chemia Corporation
- 0.07 grams of FD&C Blue #1
- 89.7 grams of water.

The resulting concentrate is 6.6 weight percent phospholipid; 1.32 weight percent isopropyl alcohol; 2.31 weight percent of fragrance; 0.07 weight percent color; and 89.7 weight percent water.

EXAMPLE 2

A toilet flushing fluid concentrate was prepared according to the following formula:
- 20 grams of Phospholipid PTCT from Mona Industries, Inc.
- 2 grams of isopropyl alcohol
- 7 grams of Spice Fragrance #2207 from Chemia Corporation
- 0.07 grams of FD&C Blue #1
- 3.0 grams of Surfonic N95
- 67.93 grams of water The resulting concentrate is 20.0 weight phospholipid; 2.0 weight percent isopropyl alcohol; 7.0 weight percent fragrance; 0.07 weight percent color; 3.0 weight percent detergent; and 67.93 weight percent water.

EXAMPLE 3

A toilet flushing concentrate prepared according to the following formula:
- 6.5 grams of Phospholipid PTC™ from Mona Industries, Inc.
- 1.3 grams of isopropyl alcohol
- 4.0 grams of Clean & Fresh™ Fragrance #2257 from Chemia Corporation
- 0.6 grams of Acid Blue #9
- 0.25 grams of triclosan
- 87.35 grams of water The resulting concentrate was 6.5 weight percent phospholipid; 1.3 weight percent isopropyl alcohol; 4.0 weight percent fragrance; 0.6 weight percent color; and 0.25 triclosan; and 87.35 weight percent water.

EXAMPLE 4

A toilet flushing fluid concentrate was prepared according to the following formula:
- 7.0 grams of Phospholipid CDW™ from Mona Industries, Inc.
- 4.0 grams of isopropyl alcohol
- 20 grams of Citrus Fragrance #3053 from Chemia Corporation
- 0.07 grams of FD&C Blue #1
- 1.0 gram of Surfonic N120
- 85.93 grams of water The resulting concentrate is 7.0 weight percent phospholipid; 4.0 weight percent isopropyl alcohol; 3.5 weight percent fragrance; 0.07 weight percent color; 1.0 weight percent detergent; and 85.93 weight percent water.

EXAMPLE 5

A toilet flushing fluid concentrate was prepared according to the following formula:
- 8.0 grams of Phospholipid CDM from Mona Industries, Inc.
- 4.0 grams of isopropyl alcohol
- 3.5 grams of Spice Fragrance #2207 from Chemia corporation
- 0.5 grams of ethylene glycol mono phenyl ether
- 1.0 gram of Surfonic N120
- 0.07 grams of FD&C Blue #1
- 82.97 grams of water The resulting concentrate is 8.0 weight percent phospholipid, 4.0 weight percent isopropyl alcohol, 3.5 weight percent fragrance; 0.5 weight percent anti-microbial; 1 weight percent detergent; 0.07 weight percent color; and 82.97 weight percent water.

EXAMPLE 6

A toilet flushing concentrate prepared according to the following formula:
- 6.0 grams of Phospholipid CDM from Mona Industries, Inc.
- 4.0 grams of isopropyl alcohol
- 4.0 grams of citronella oil
- 0.60 grams of Acid Blue #9
- 0.25 grams of triclosan
- 1.0 grams of Surfonic N120
- 84.15 grams of water The resulting concentrate is 6.0 weight percent phospholipid, 4.0 weight percent isopropyl alcohol, 4.0 weight percent fragrance (oil), 0.6 weight percent of Acid Blue #9; 0.25 weight percent anti-microbial agent; 1.0 weight percent detergent, and 84.15 weight percent water.

Test

The concentrate of Example 1 was tested to determine its ability to control odors. The concentrate was diluted at a ratio of 1:128 with tap water to form a test fluid. At time zero, 200 mls of fresh raw sewage was added to 400 mls of the test fluid to create 600 mls of sample fluid at a dilution of 1:1.5. At the same time a control was prepared by mixing four parts of the fresh raw sewage with one part of tap water. After 30 minutes, the 1:1.5 sample fluid was divided into two equal portions of 300 mls each, and 100 mls of fresh raw sewage was added to one of these portions to create 400 mls of sample fluid at a dilution of 1:2. After 60 minutes, the 1:2 sample fluid was divided into two equal portions of 200 mls each, and 300 mls of fresh raw sewage was added to one of these portions to create 500 mls of a sample fluid at a dilution of 1:5. The sample fluids and the control were then incubated on a shaker at 35° C. Total microbial counts (organisms per ml) and total coliform counts (organisms/100 ml) were made of the various samples using standard techniques. These counts are tabulated in Table A:

| TOTAL MICROBIAL COUNT | | | | | | |
|---|---|---|---|---|---|---|
| DILUTION | 0 hr | 1 hr | 3 hrs | 5 hrs | 24 hrs | 48 hrs |
| 1:1.5 | $1 \times 10^6$ | $1 \times 10^4$ | $3 \times 10^3$ | $8 \times 10^2$ | $2 \times 10^2$ | $8 \times 10^1$ |
| 1:2.0 | $5 \times 10^6$ | $3 \times 10^6$ | $1 \times 10^6$ | $8 \times 10^5$ | $4 \times 10^4$ | $8 \times 10^3$ |
| 1:5.0 | $6 \times 10^7$ | $4 \times 10^7$ | $4 \times 10^7$ | $7 \times 10^6$ | $1 \times 10^6$ | $8 \times 10^5$ |
| CONTROL | $8 \times 10^8$ | $3 \times 10^9$ | $4 \times 10^{10}$ | $8 \times 10^{11}$ | $9 \times 10^{12}$ | $6 \times 10^{13}$ |

This information is indicated graphically in FIG. 1, showing that the diluted fluid affects the total microbial population, as compared with the control.

| TOTAL COLIFORM COUNT | | | | | | |
|---|---|---|---|---|---|---|
| DILUTION | 0 hr | 1 hr | 3 hrs | 5 hrs | 24 hrs | 48 hrs |
| 1:1.5 | $1 \times 10^5$ | $1 \times 10^3$ | $6 \times 10^2$ | $4 \times 10^2$ | $8 \times 10^1$ | $1 \times 10^1$ |
| 1:2.0 | $8 \times 10^6$ | $4 \times 10^6$ | $3 \times 10^4$ | $2 \times 10^4$ | $1 \times 10^4$ | $7 \times 10^2$ |
| 1:5.0 | $1 \times 10^8$ | $1 \times 10^7$ | $3 \times 10^6$ | $2 \times 10^6$ | $2 \times 10^5$ | $1 \times 10^3$ |
| CONTROL | $7 \times 10^8$ | $2 \times 10^9$ | $5 \times 10^9$ | $9 \times 10^9$ | $2 \times 10^{10}$ | $1 \times 10^{11}$ |

Figure 2:
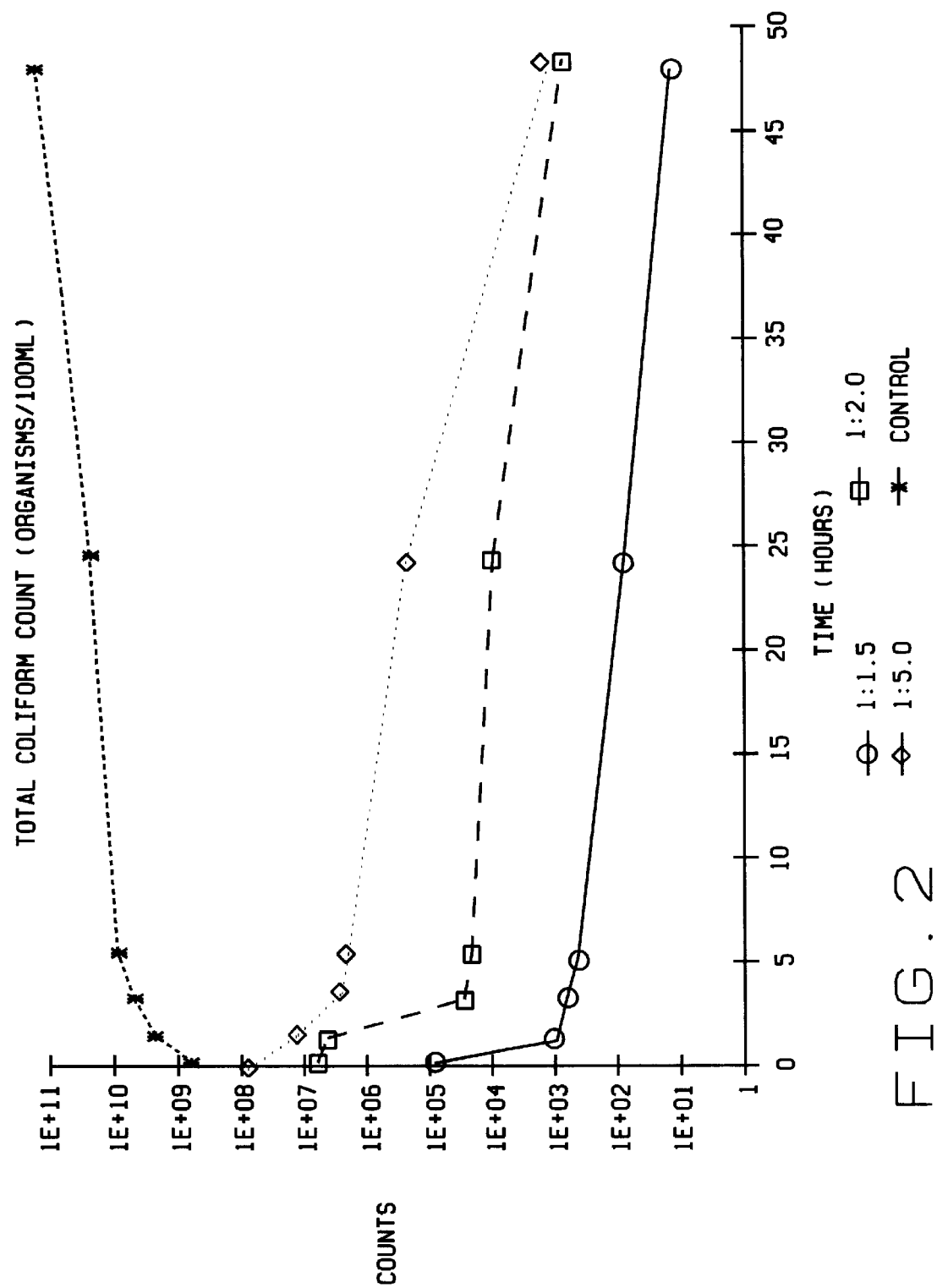
FIG. 2 is a graph of coliform counts in various dilutions of a flushing fluid according to the principles of the present invention, showing the ability of these flushing fluids to control microbes.

This information is indicated graphically in FIG. 2, showing that the diluted fluid affects the total coliform count, as compared with the control.

The 1:5 sample and the control were subjectively evaluated for order control on the following scale: 0=no odor; 1=slight odor; 2=moderate odor; 3=strong odor; and 4=very strong odor. The results are given in the table:

| ODOR TEST | | | | | | |
|---|---|---|---|---|---|---|
| DILUTION | 0 hr | 1 hr | 3 hrs | 5 hrs | 24 hrs | 48 hrs |
| 1:5.0 | 2 | 2 | 2 | 2 | 2 | 2 |
| CONTROL | 4 | 4 | 4 | 4 | 4 | 4 |

This shows that the diluted fluid is effective in controlling odors.

The fluid concentrates of the several examples are adapted for use in closed toilet systems. The concentrate can be diluted in a ratio of 1:128 (e.g, one ounce in one gallon of water). The phospholipids help kill or inhibit bacteria in the fluid to reduce or delay the formation of odors in the fluid so that the fluid can be recirculated. Additional anti-microbial agents can be included in the fluid to help control odor-causing microbes. The detergent increases the cleaning action of the fluid. The fragrance masks odors that do occur and the color also masks contaminants in the fluids. The fluid is non-corrosive and is well tolerated by human skin. However, when the used fluid is disposed of, the phospholipid is sufficiently diluted that it loses its bacteriostatic properties and becomes biodegradable. Thus while in use concentrations the phospholipids exhibit odor control capabilities, when diluted the phospholipids readily degrade.

From the foregoing, it will be seen that this invention is one well adapted to attain all the ends and objectives hereinabove set forth, together with advantages that are obvious and that are inherent to the invention. It will be understood that certain features and sub-combinations are of utility and can be employed without reference to other features and sub-combinations. This is contemplated by and is within the scope of the claims. Because many possible embodiments can be made of the invention without departing from the scope thereof, it is to be understood that all matter herein set forth is to be interpreted as illustrative and not in a limiting sense.

What is claimed is:

1. A method for deodorizing a closed toilet system of the type that recirculates the flushing fluid, the method comprising the step of adding an aqueous solution comprising a first antimicrobial agent, a second antimicrobial agent, and an alcohol to the flushing fluid in a concentration effective to inhibit odor-causing bacteria, said first antimicrobial agent comprising a phospholipid and said second antimicrobial agent comprising 5-chloro-2-(2,4-dichlorophenoxy) phenol or ethylene glycol mono phenyl ether.

2. The method in accordance with claim 1 wherein the phospholipid is cocamidopropylphosphatidyl polypropylene glycol-dimonium chloride.

3. The method in accordance with claim 1 wherein the phospholipid is cocophosphatidyl polypropylene glycol-dimonium chloride.

4. The method in accordance with claim 1 further comprising the step of adding a fragrance to the flushing fluid.

5. The method in accordance with claim 1 wherein said step of adding an aqueous solution to the flushing fluid comprises the step of adding a flushing fluid concentrate comprising a first antimicrobial agent, a second antimicrobial agent, and an alcohol to the flushing fluid.

6. The method in accordance with claim 5 wherein the alcohol comprises isopropanol.

7. The method in accordance with claim 5 wherein the concentrate further includes a colorant.

8. The method in accordance with claim 5 wherein the concentrate further comprises a detergent.

9. A method for deodorizing the flushing fluid in a closed toilet system in which the flushing fluid is recirculated, the method comprising the steps of:

forming an aqueous solution comprising a first antimicrobial agent, a second antimicrobial agent, and an alcohol, said first antimicrobial agent comprising a phospholipid and said second antimicrobial agent comprising 5-chloro-2-(2,4-dichlorophenoxy) phenol or ethylene glycol mono phenyl ether; and adding the aqueous solution to the flushing fluid in a concentration effective to inhibit odor-causing bacteria.

10. The method in accordance with claim 9 wherein the phospholipid is cocamidopropylphosphatidyl polypropylene glycol-dimonium chloride.

11. The method in accordance with claim 9 wherein the phospholipid is cocophosphatidyl polypropylene glycol-dimonium chloride.

12. The method in accordance with claim 9 further comprising the step of adding a fragrance to the aqueous solution.

13. The method in accordance with claim 9 wherein said step of forming an aqueous solution comprises the step of forming a flushing fluid concentrate.

14. The method in accordance with claim 13 wherein said step of adding the aqueous solution comprises the step of adding the flushing fluid concentrate to the flushing fluid in a concentration effective to inhibit odor-causing bacteria.

15. The method in accordance with claim 14 wherein said step of forming a flushing fluid concentrate comprises the step of adding a fragrance to the concentrate.

16. The method in accordance with claim 14 wherein the alcohol comprises isopropanol.

17. The method in accordance with claim 14 wherein said step of forming a flushing fluid concentrate comprises the step of adding a colorant to the concentrate.

18. The method in accordance with claim 14 wherein said step of forming a flushing fluid concentrate comprises the step of adding a detergent to the concentrate.

19. A flushing fluid concentrate adapted to be added to a flushing fluid in a closed toilet system, said flushing fluid concentrate for controlling odors in the flushing fluid, said concentrate comprising an aqueous solution comprising a first antimicrobial agent, a second antimicrobial agent, and an alcohol in an amount sufficient to inhibit odor-causing bacteria, said first antimicrobial agent comprising a phospholipid and said second antimicrobial agent comprising 5-chloro-2-(2,4-dichlorophenoxy) phenol or ethylene glycol mono phenyl ether.

20. The concentrate in accordance with claim 19 wherein said alcohol comprises isopropanol.

21. The concentrate in accordance with claim 19 wherein said phospholipid is cocamidopropylphosphatidyl polypropylene glycol-dimonium chloride.

22. The concentrate in accordance with claim 19 wherein said phospholipid is cocophosphatidyl polypropylene glycol-dimonium chloride.

23. The concentrate in accordance with claim 19 further comprising a fragrance.

24. The concentrate in accordance with claim 19 further comprising a colorant.

25. The concentrate in accordance with claim 19 further comprising a detergent.

* * * * *